(12) United States Patent
Kim et al.

(10) Patent No.: US 11,480,675 B2
(45) Date of Patent: Oct. 25, 2022

(54) PHOTOACOUSTIC APPARATUS, AND APPARATUS AND METHOD FOR OBTAINING PHOTOACOUSTIC IMAGE

(71) Applicants: SAMSUNG ELECTRONICS CO., LTD., Suwon-si (KR); POSTECH Research and Business Development Foundation, Pohang-si (KR)

(72) Inventors: Chulhong Kim, Pohang-si (KR); Jin Young Kim, Pohang-si (KR); Hyojin Kim, Daegu (KR); Jin Woo Baik, Daejeon (KR); Joongho Ahn, Pohang-si (KR)

(73) Assignees: SAMSUNG ELECTRONICS CO., LTD., Suwon-si (KR); POSTECH Research and Business Development Foundation, Pohang-si (KR)

( * ) Notice: Subject to any disclaimer, the term of this patent is extended or adjusted under 35 U.S.C. 154(b) by 0 days.

(21) Appl. No.: 17/206,358

(22) Filed: Mar. 19, 2021

(65) Prior Publication Data

US 2022/0155259 A1    May 19, 2022

(30) Foreign Application Priority Data

Nov. 19, 2020   (KR) .................... 10-2020-0155778

(51) Int. Cl.
*G01S 15/89* (2006.01)
*G01N 29/24* (2006.01)
(Continued)

(52) U.S. Cl.
CPC ...... *G01S 15/8965* (2013.01); *G01N 29/2425* (2013.01); *G10K 11/205* (2013.01);
(Continued)

(58) Field of Classification Search
CPC ............ G01S 15/8965; G01N 29/2425; G01N 29/44; G01N 2291/101; G10K 11/205;
(Continued)

(56) References Cited

U.S. PATENT DOCUMENTS 7,861,574 B2   1/2011   Sheen et al.
8,454,512 B2   6/2013   Wang et al.
(Continued)

FOREIGN PATENT DOCUMENTS

JP    2014-072506 A    4/2014
KR    10-1749602 B1    6/2017
(Continued)

*Primary Examiner* — Lisa M Caputo
*Assistant Examiner* — Rose M Miller
(74) *Attorney, Agent, or Firm* — Sughrue Mion, PLLC

(57) ABSTRACT

A photoacoustic apparatus may include: a ring transducer configured to measure a photoacoustic signal generated from an object, and including a hollow space that is provided as a travel path of light and ultrasonic waves; a mirror part disposed along a light path of the light transmitted from the ring transducer, and configured to reflect the light transmitted from the ring transducer, and the ultrasonic waves generated from the object, and to adjust magnification of the mirror part according to a number of apertures of the photoacoustic apparatus; and a fluid tank including a transparent film that allows the photoacoustic signal to pass through the fluid tank, and accommodating a fluid, the ring transducer, and the mirror part inside the fluid tank.

20 Claims, 17 Drawing Sheets

(51) Int. Cl.
*G10K 11/20* (2006.01)
*G10K 11/28* (2006.01)
*G10K 11/30* (2006.01)
*G01N 29/44* (2006.01)
*G10K 11/18* (2006.01)
*G10K 11/26* (2006.01)

(52) U.S. Cl.
CPC .............. *G10K 11/28* (2013.01); *G10K 11/30* (2013.01); *G01N 29/44* (2013.01); *G01N 2291/101* (2013.01); *G10K 11/18* (2013.01); *G10K 11/20* (2013.01); *G10K 11/26* (2013.01)

(58) Field of Classification Search
CPC ........ G10K 11/28; G10K 11/30; G10K 11/18; G10K 11/20; G10K 11/26
USPC .......................................................... 73/643
See application file for complete search history.

(56) References Cited

U.S. PATENT DOCUMENTS

| | | |
|---|---|---|
| 9,131,877 B2 | 9/2015 | Ichihara |
| 9,351,705 B2 | 5/2016 | Wang et al. |
| 9,874,545 B2 | 1/2018 | Fukushima et al. |
| 10,653,321 B2 | 5/2020 | Wang et al. |
| 2018/0078143 A1 | 3/2018 | Pramanik et al. |
| 2019/0320999 A1 | 10/2019 | Bae et al. |
| 2020/0173965 A1 | 6/2020 | Sangu |
| 2020/0397404 A1 | 12/2020 | Oak et al. |
| 2021/0186411 A1* | 6/2021 | Wang ................. G02B 26/0833 |
| 2022/0054001 A1* | 2/2022 | Zhu ........................ A61B 5/742 |

FOREIGN PATENT DOCUMENTS

| | | | |
|---|---|---|---|
| KR | 10-1936120 B1 | 1/2019 | |
| KR | 10-2011975 B1 | 8/2019 | |
| KR | 20200024421 A * | 3/2020 | ............. G02B 7/182 |
| KR | 20200087119 A * | 7/2020 | ............ A61B 5/0095 |

* cited by examiner

PHOTOACOUSTIC APPARATUS, AND APPARATUS AND METHOD FOR OBTAINING PHOTOACOUSTIC IMAGE

CROSS-REFERENCE TO RELATED APPLICATION(S)

This application claims priority from Korean Patent Application No. 10-2020-0155778, filed on Nov. 19, 2020, in the Korean Intellectual Property Office, the disclosure of which is incorporated herein by reference in its entirety.

BACKGROUND

1. Field

The following description relates to a photoacoustic apparatus, and more particularly to a photoacoustic microscope apparatus capable of adjusting magnification, and a method of obtaining photoacoustic images.

2. Description of the Related Art

Photoacoustic microscopy is a next generation medical imaging technique and is recently receiving attention in various fields of preclinical and clinical research as a hybrid imaging technique that combines optical and ultrasonic imaging methods. A photoacoustic microscope system acquires three-dimensional (3D) images of a desired target portion by emitting a laser beam onto the target portion to be examined, and by measuring ultrasonic waves generated according to an amount of the laser light absorbed by the target. Unlike computerized tomography (CT) or X-ray imaging, the photoacoustic microscope system provides images without using ionizing radiation, and may be implemented rapidly at a low cost compared to MRI or PET. Further, the photoacoustic microscope system may obtain images at a deeper depth compared to optical images, as well as may obtain functional information such as blood oxygen saturation levels and the like which may not be obtained from ultrasonic imaging data. By obtaining a variety of pathological information based on light absorption properties of body tissue, the photoacoustic microscope system may serve as an image platform for preclinical and clinical studies on small animals.

SUMMARY

According to an aspect of an example embodiment, there is provided a photoacoustic apparatus, including: a ring transducer configured to measure a photoacoustic signal generated from an object, and including a hollow space that is provided as a travel path of light and ultrasonic waves; a mirror part disposed along a light path of the light transmitted from the ring transducer, and configured to reflect the light transmitted from the ring transducer, and the ultrasonic waves generated from the object, and to adjust magnification of the mirror part according to a number of apertures of the photoacoustic apparatus; and a fluid tank including a transparent film that allows the photoacoustic signal to pass through the fluid tank, and accommodating a fluid, the ring transducer, and the mirror part inside the fluid tank.

The mirror part may include a parabolic mirror set of a plurality of parabolic mirrors having different magnification levels and disposed on one surface of a support part of the photoacoustic apparatus.

The mirror part may include a turning part disposed on another surface of the support part and protruding outside of the fluid tank, and configured to rotate to adjust the magnification of the parabolic mirror set.

The fluid tank may include an installation hole, into which parabolic mirrors are inserted, and the mirror part may include the parabolic mirrors having different magnification levels and being replaceable through the installation hole of the fluid tank.

The mirror part may include a stopper which is coupled to the parabolic mirror, and supports the parabolic mirror when the parabolic mirror is inserted into the fluid tank.

The stopper may include at least one of an O-ring and a bearing to fix the parabolic mirror.

The photoacoustic apparatus may further include a motor coupled to one surface of the mirror part outside of the fluid tank, and may be configured to control a position of the mirror part or to reciprocate or rotate the mirror part.

The photoacoustic apparatus may further include a photoacoustic scanner disposed between the mirror part and the object on the light path, and may be configured to reflect the light transmitted from the mirror part toward the object, and to reflect the ultrasonic waves generated from the object toward the mirror part.

The ring transducer may be a focal ring transducer having an acoustic lens to align the light and the ultrasonic waves at a same height.

According to an aspect of another example embodiment, there is provided a photoacoustic apparatus, including: an ultrasonic transducer configured to measure a photoacoustic signal generated from an object; a mirror part disposed along a light path of light transmitted from the ultrasonic transducer, and configured to reflect the light transmitted from the ultrasonic transducer, and the ultrasonic waves generated from the object, and to adjust magnification of the mirror part according to a number of apertures of the photoacoustic apparatus; a photoacoustic coupling part disposed to come into contact with the ultrasonic transducer, and configured to reflect the light transmitted from a light source toward the mirror part, and to pass the photoacoustic signal, which is generated from the object, toward the ultrasonic transducer; and a fluid tank including a transparent film that allows the photoacoustic signal to pass through the fluid tank, and accommodating a fluid, the transducer, and the mirror part inside the fluid tank.

According to an aspect of another example embodiment, there is provided an image obtaining apparatus including: a light source configured to supply light; a photoacoustic apparatus configured to emit the supplied light onto an object, and to detect a photoacoustic signal generated by the object after the light is absorbed into the object; an amplifier configured to amplify the photoacoustic signal detected by the photoacoustic apparatus; a processor configured to obtain image data by performing image processing on the amplified photoacoustic signal; and a driver configured to drive the photoacoustic apparatus, wherein the photoacoustic apparatus may include: a ring transducer configured to transmit the light supplied from the light source, and to measure the photoacoustic signal generated from the object, and including a hollow space that is provided as a travel path of the light and ultrasonic waves; a mirror part disposed along a light path of the light transmitted from the ring transducer, and configured to reflect the light transmitted from the ring transducer, and the ultrasonic waves generated from the object, and to adjust magnification of the photoacoustic apparatus according to a number of apertures of the photoacoustic apparatus; and a fluid tank including a transparent film that allows the photoacoustic signal to pass through the fluid thank, and accommodating a fluid, the ring transducer, and the mirror part inside the fluid tank.

The light may be a collimator beam.

The mirror part may include a parabolic mirror set of a plurality of parabolic mirrors having different magnification levels and disposed on one surface of a support part.

The mirror part may include a turning part disposed on the other surface of the support part and protruding outside of the fluid tank to be rotated to adjust the magnification of the parabolic mirror set of the photoacoustic apparatus.

The fluid tank may include an installation hole, into which parabolic mirrors are inserted, and the mirror part may include the parabolic mirrors having different magnification levels and being replaceable through the installation hole of the fluid tank.

The mirror part may include a stopper which is coupled to the parabolic mirror, such that when the parabolic mirror is inserted into the fluid tank, the stopper supports the parabolic mirror.

The photoacoustic apparatus may include a motor coupled to one surface of the mirror part outside of the fluid tank, and may be configured to control a position of the mirror part or to reciprocate or rotate the mirror part.

According to an aspect of another example embodiment, there is provided a method of obtaining a photoacoustic image using a photoacoustic apparatus, the method including: adjusting magnification of a mirror part according to a number of apertures; supplying light by a light source; passing the light, which is supplied from the light source, through a ring transducer; by the mirror part, reflecting the light transmitted from the ring transducer toward an object; by the mirror part, reflecting ultrasonic waves generated from the object toward the ring transducer; by the ring transducer, aligning the light and the ultrasonic waves along a single path; by the ring transducer, measuring a photoacoustic signal generated from the object; by an amplifier, amplifying the photoacoustic signal measured by the ring transducer; and by a processor, obtaining image data by performing image processing on the photoacoustic signal amplified by the amplifier.

The adjusting the magnification may include: adjusting the magnification of the mirror part by rotating a turning part of the photoacoustic apparatus that is coupled to the mirror part.

The aligning the light and the ultrasonic waves may include aligning the light and the ultrasonic waves at a same height by using an acoustic lens included in the ring transducer.

Figure 1:
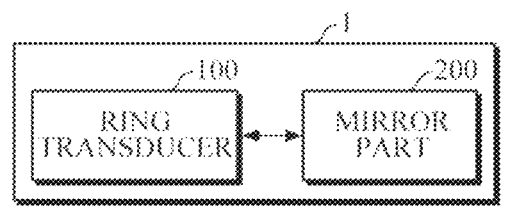
FIG. 1 is a block diagram illustrating a photoacoustic apparatus according to an embodiment of the present disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of other embodiments are included in the following detailed description and drawings. Advantages and features of the present invention, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of a photoacoustic apparatus, and an apparatus and method for obtaining a photoacoustic image will be described with reference to the accompanying drawings.

FIG. 1 is a block diagram illustrating a photoacoustic apparatus according to an embodiment of the present disclosure.

Referring to FIG. 1, the photoacoustic apparatus 1 includes a ring transducer 100 and a mirror part 200.

The ring transducer 100 measures a photoacoustic signal generated from an object, and has a hollow space at the center thereof, so that light and ultrasonic waves may be aligned along a single path.

The ring transducer 100 may include a focal ring transducer or a non-focal ring transducer.

The mirror part 200 may be disposed perpendicular to the ring transducer 100 on a light path. The mirror part 200 may reflect light, transmitted from the ring transducer 100, and may also reflect ultrasonic waves generated from the object. The mirror part 200 may adjust magnification according to a desired or preset number of apertures.

The ring transducer 100 and the mirror part 200 may be included in a water tank (e.g., reference 500 in FIG. 2A) containing a fluid. In this case, the fluid may be water but is not limited thereto, and the water tank may be also referred to as a fluid tank. Further, the water tank may have a transparent film or a transparent membrane (e.g., reference 600 in FIG. 2A) so as to allow the photoacoustic signal to pass therethrough.

Light, transmitted from a light source, may pass through the ring transducer 100 to be reflected from the mirror part 200 and then may be emitted onto the object through the transparent film. A photoacoustic image may be obtained in such a manner that the ultrasonic waves generated from the object are transmitted to the mirror part 200 through the transparent film, to be reflected from the mirror part 200 and transmitted to the ring transducer 100.

For example, the mirror part 200 may include a support part. The mirror part 200 may include a set of a plurality of parabolic mirrors disposed on one surface of the support part and having different magnification levels. In addition, the mirror part 200 may include a turning part. The turning part may be disposed on the other surface of the support part, and may protrude outside of the water tank to be rotated to adjust the magnification levels of the parabolic mirror set of the plurality of parabolic mirrors.

In yet another example, the water tank may have an installation hole, into which the parabolic mirror may be inserted. Further, the mirror part 200 may include the plurality of parabolic mirrors having different magnification levels and being replaceable along the installation hole formed in the water tank.

The mirror part 200 may include a stopper. The stopper is coupled to the parabolic mirror, such that when the parabolic mirror is inserted into the water tank, the stopper may support the parabolic mirror. In this case, the parabolic mirror and the stopper may be integrally formed with each other or may be detachable from each other. However, the arrangement is not limited thereto.

In addition, the photoacoustic apparatus 1 may further include a motor. The motor may be coupled to the mirror part 200 to precisely control the position of the parabolic mirror or may rotate the parabolic mirror rapidly. In this manner, light emitted onto a sample and the generated photoacoustic signal may be scanned at the same time, such that a B-scan image may be obtained rapidly.

Moreover, the photoacoustic apparatus 1 may further include a photoacoustic scanner. The photoacoustic scanner is disposed between the mirror part 200 and the object on the light path and may reflect light, transmitted from the mirror part 200, to the object and may reflect ultrasonic waves, generated from the object, to the mirror part 200.

Figure 2A:
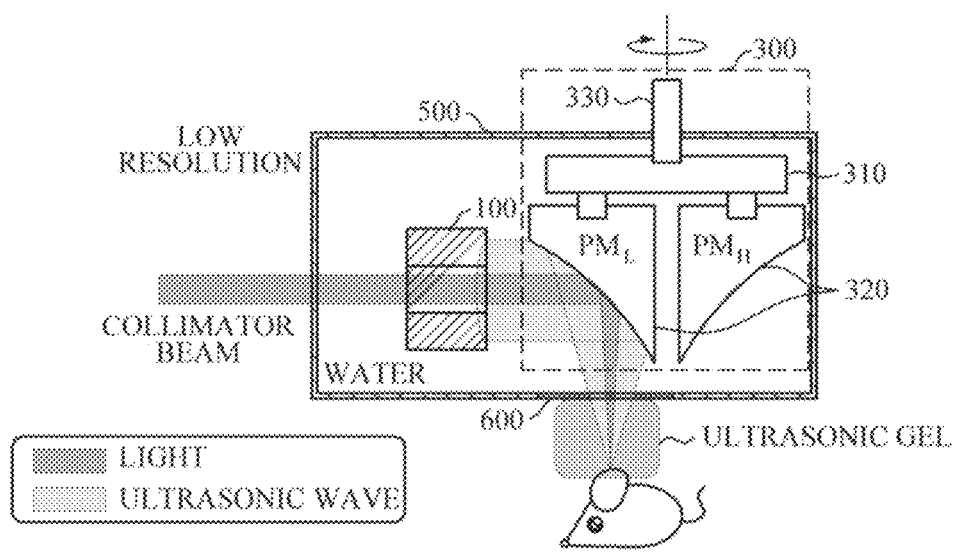
FIGS. 2A and 2B are diagrams illustrating an example of a photoacoustic apparatus which is rotatable to adjust magnification of a parabolic mirror.
Figure 2B:
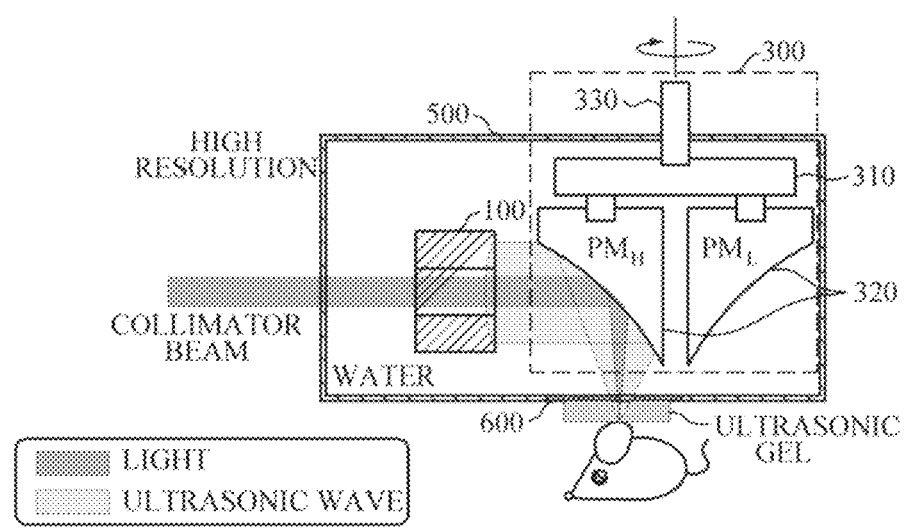

FIGS. 2A and 2B are diagrams illustrating an example of a photoacoustic apparatus which is rotatable to adjust magnification of parabolic mirrors.

Referring to FIGS. 2A and 2B, a mirror part 300 according to an embodiment may include a support part 310. The mirror part 300 may include a parabolic mirror set 320 of a plurality of parabolic mirrors having different magnification levels. The parabolic mirror set 320 of the plurality of parabolic mirrors may be disposed on one surface of the support part 310. A turning part 330 is disposed on the other surface of the support part 310 and protrudes outside of the water tank 500 to be rotated to adjust magnification of the parabolic mirrors. The water thank 500 may include a transparent film 600 to allow a photoacoustic signal to pass through the water thank 500.

FIGS. 2A and 2B illustrate an example of adjusting magnification by rotating the turning part 330 coupled to the support part 310.

Specifically, FIG. 2A illustrates a case of observation at a low magnification, and FIG. 2B illustrates a case of observation at a high magnification. Referring to FIG. 2A, observation with low resolution is performed in such a manner that the turning part 330 is rotated so that a parabolic mirror PML having a low magnification is disposed on a light path, and light is emitted accordingly. Referring to FIG. 2B, observation with high resolution is performed in such a manner that the turning part 330 is rotated so that a parabolic mirror PML having a high magnification is disposed on a light path, and light is emitted accordingly.

The support part 310 may be formed in various shapes, such as a straight bar, a cross-shaped bar, a circular shape, etc., according to the arrangement of the parabolic mirrors 320.

While FIGS. 2A and 2B illustrate only the parabolic mirror PML having a low magnification and the parabolic mirror PML having a high magnification, but the parabolic mirror is not limited thereto, and the parabolic mirror set 320 of the plurality of parabolic mirrors may include three or more parabolic mirrors having different magnification levels.

In addition, the photoacoustic apparatus 1 may further include a motor. The motor may be coupled to the turning part 330 while being in contact with an upper end of the turning part 330. The motor may rotate the turning part 330 so that a parabolic mirror to be disposed on the light path may be selected from the parabolic mirror PML having a low magnification and the parabolic mirror PML having a high magnification.

The motor may rotate the turning part 330 to precisely control the position of the parabolic mirror 320 or may rotate the parabolic mirror 320 rapidly. In this manner, light emitted onto a sample and the generated photoacoustic signal may be scanned at the same time, such that a B-scan image may be obtained rapidly.

In another example, the photoacoustic apparatus 1 may further include a photoacoustic scanner. The photoacoustic scanner may be disposed between the mirror part and the object on the photoacoustic light path, and may reflect light, transmitted from the mirror part, to the object and may reflect ultrasonic waves, generated from the object, to the mirror part.

Accordingly, observation may be performed by adjusting the light path not only in the case where the object is located at a lower end of the water tank, but also in the case where the object is located on a side surface of the water tank. In addition, by further providing the photoacoustic scanner, a scanning speed may be increased.

Figure 3:
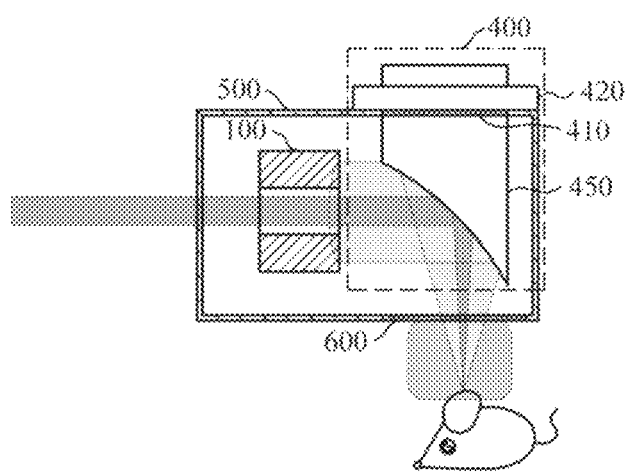
FIGS. 3, 4A, and 4B are diagrams illustrating an example of a photoacoustic apparatus in which a parabolic mirror is replaceable.
Figure 4A:
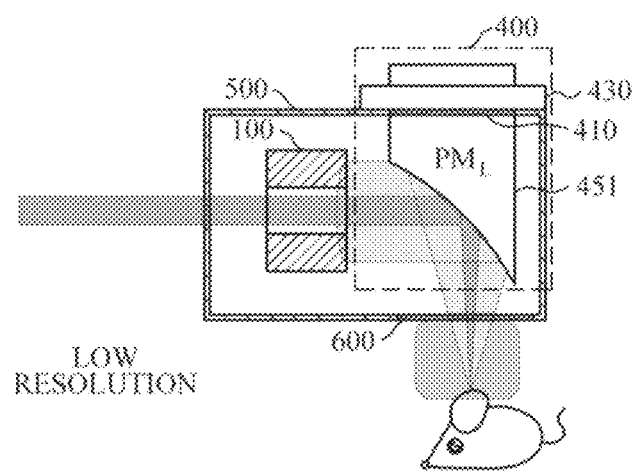
Figure 4B:
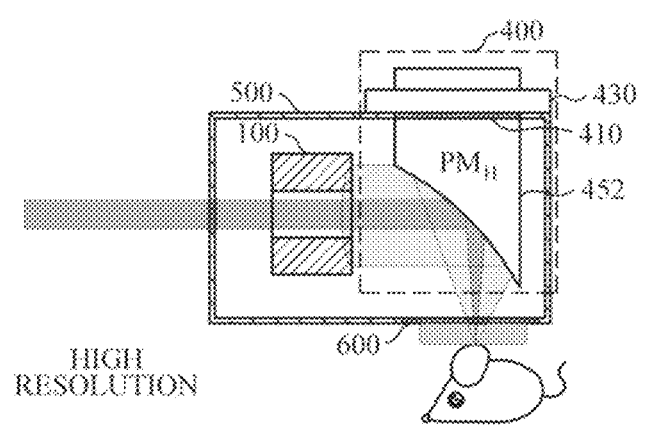

FIGS. 3, 4A, and 4B are diagrams illustrating an example of a photoacoustic apparatus in which a parabolic mirror is replaceable.

Referring to FIG. 3, a water tank 500 has an installation hole 410, into which a parabolic mirror 450 may be inserted. Further, the parabolic mirror 450 may be replaced with parabolic mirrors having different magnification levels along the installation hole 410 formed in the water tank 500.

The mirror part 400 may include a stopper 420. The stopper 420 may be coupled to the parabolic mirror 450, such that when the parabolic mirror 450 is inserted into the water tank 500, the stopper 420 may support the parabolic mirror 450. In this case, the parabolic mirror 450 and the stopper 420 may be integrally formed with each other or may be detached from each other.

Specifically, referring to FIG. 4A, a parabolic mirror 451 having a low magnification is inserted along the installation hole 410, and the stopper 430 supports the parabolic mirror 451. Referring to FIG. 4A, instead of the parabolic mirror 451 having a low magnification, a parabolic mirror 452 having a high magnification is inserted. This shows that by replacing the parabolic mirrors 451 and 452 along the installation hole 410 formed in the water tank 500, magnification may be adjusted simply.

The stopper 430 of FIGS. 4A and 4B may include an O-ring, a bearing, and the like, but is not limited thereto.

The photoacoustic apparatus of FIGS. 3, 4A, and 4B may be manufactured in a compact size with a replaceable parabolic mirror, compared to the photoacoustic apparatus which is rotated to adjust magnification.

Figure 5A:
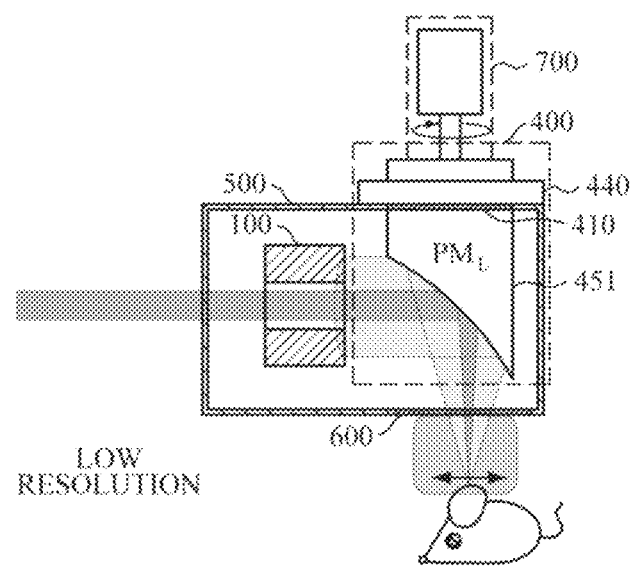
FIGS. 5A and 5B are diagrams illustrating an example in which a motor is coupled to a mirror part.
Figure 5B:
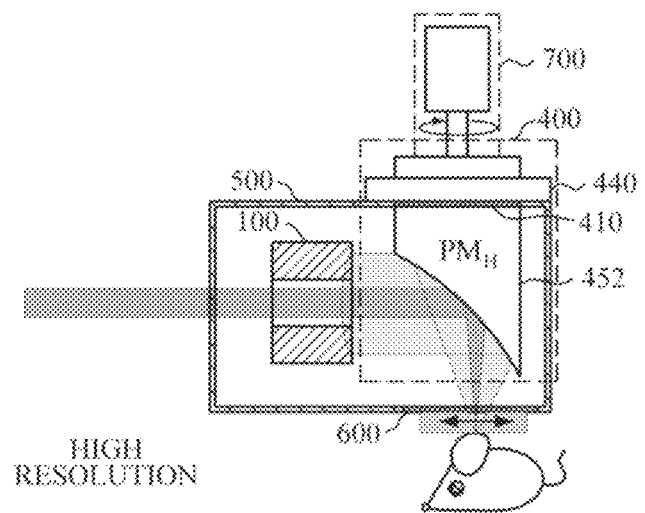

FIGS. 5A and 5B are diagrams illustrating an example in which a motor is coupled to a mirror part.

FIG. 5A illustrates an example in which the parabolic mirror 451 having a low magnification is coupled to a motor 700; and FIG. 5B illustrates an example in which the parabolic mirror 452 having a high magnification is coupled to the motor 700.

The motor 700 may be coupled to an upper end of the respective mirrors 451 and 452.

The motor 700 may reciprocate or rotate the parabolic mirrors 451 and 452. In other words, the motor 700 may precisely control a specific position, at which light having passed through the transducer 100 is to be reflected from the parabolic mirrors 451 and 452.

Further, the motor 700 may allow the parabolic mirrors 451 and 452 to reciprocate rapidly within a predetermined angle range, such that an enhanced depth image may be obtained. In this manner, light emitted onto a sample and a generated photoacoustic signal may be scanned at the same time, such that a B-scan image may be obtained rapidly.

In this case, the stopper 440 may be formed as a bearing to facilitate rotation of the parabolic mirrors 451 and 452 by the rotation of the motor 700. However, the stopper 440 is not limited thereto.

Figure 6A:
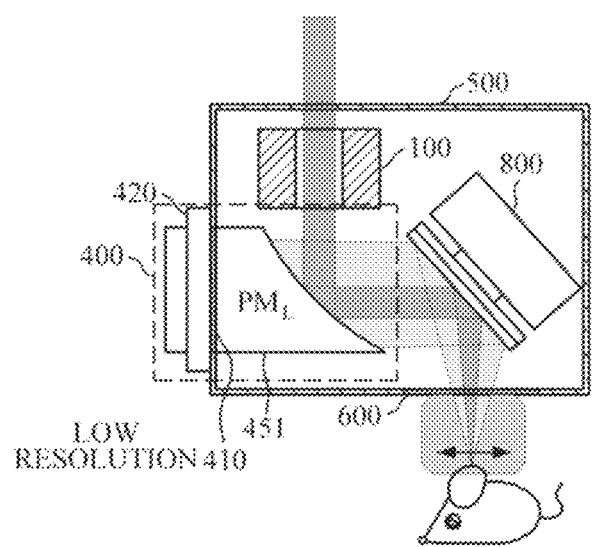
FIGS. 6A and 6B are diagrams illustrating an example in which a photoacoustic scanner is further included in a water tank.
Figure 6B:
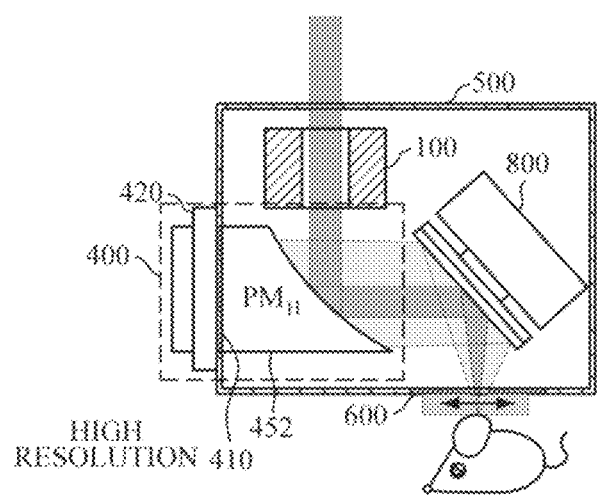

FIGS. 6A and 6B are diagrams illustrating an example in which a photoacoustic scanner is further included in a water tank.

Referring to FIGS. 6A and 6B, the photoacoustic apparatus 1 may further include a photoacoustic scanner 800. The photoacoustic scanner 800 is disposed between the mirror part 400 and the object on a light path, and may reflect light, transmitted from the mirror part 400, to the object and may reflect ultrasonic waves, generated from the object, to the mirror part 400.

By further providing the photoacoustic scanner 800, the light and ultrasonic waves may be scanned rapidly, thereby increasing a scanning speed.

FIG. 6A illustrates an example in which the photoacoustic scanner 800 reflects light, transmitted from the parabolic mirror 451 having a low magnification in the mirror part 400, toward the object and reflects ultrasonic waves, generated from the object, to the parabolic mirror 451 having a low magnification in the mirror part 400. FIG. 6B illustrates an example in which the photoacoustic scanner 800 reflects light, transmitted from the parabolic mirror 452 having a high magnification in the mirror part 400, toward the object and reflects ultrasonic waves, generated from the object, to the parabolic mirror 452 having a high magnification in the mirror part 400.

FIGS. 6A and 6B illustrate an example in which the installation hole 410 of the water tank 500, and the stopper 420 and the parabolic mirrors 451 and 452 of the mirror part 400 are disposed on a side surface of the water tank 500.

As described above, by providing the installation hole 410 of the water tank 500, and the stopper 420 and the parabolic mirrors 451 and 452 of the mirror part 400 on the side surface of the water tank, and by further including the photoacoustic scanner 800, the photoacoustic apparatus 1 may be manufactured in a compact size. However, the arrangement of the photoacoustic apparatus 1 may be changed according to the size and purpose of the photoacoustic apparatus 1 and the like.

As described above with reference to FIGS. 5A and 5B, the mirror part 400 of FIGS. 6A and 6B may be further provided with a motor.

The stopper 420 of FIGS. 6A and 6B may include an O-ring or a bearing, but is not limited thereto.

Figure 7:
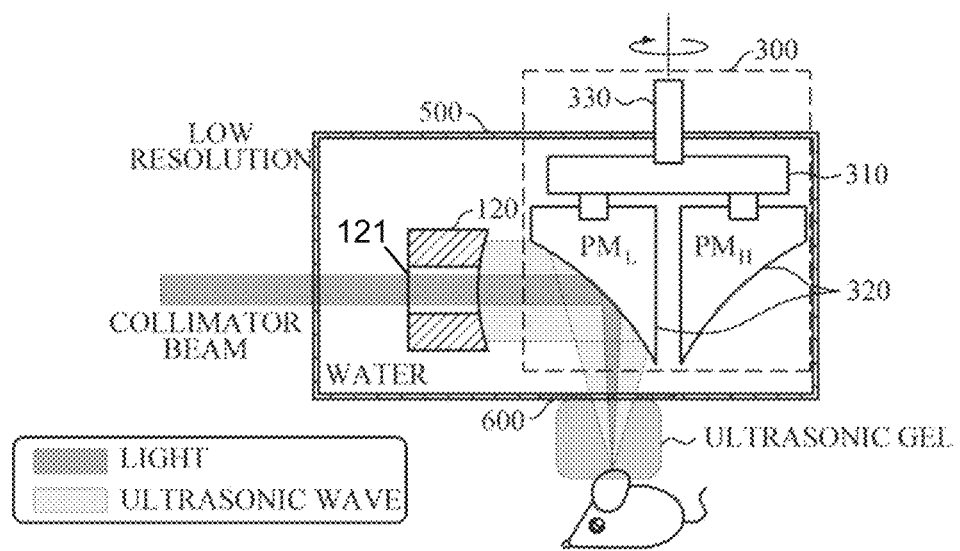
FIG. 7 is a diagram illustrating an example in which a focal ring transducer is included.

FIG. 7 is a diagram illustrating an example in which a focal ring transducer is included.

The photoacoustic apparatus 1 may include a focal ring transducer 120 including an acoustic lens 121 to align light and ultrasonic waves at the same height. However, the photoacoustic apparatus 1 is not limited thereto.

Figure 8A:
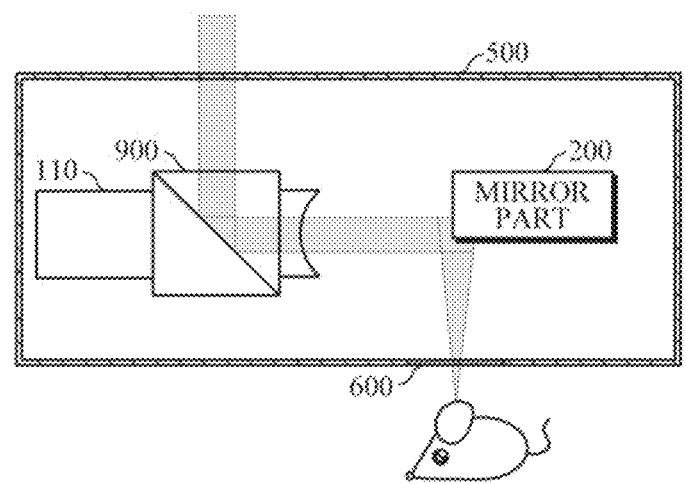
FIGS. 8A, 8B, and 8C are diagrams illustrating an example in which a photoacoustic coupling part is further included in a water tank.
Figure 8B:
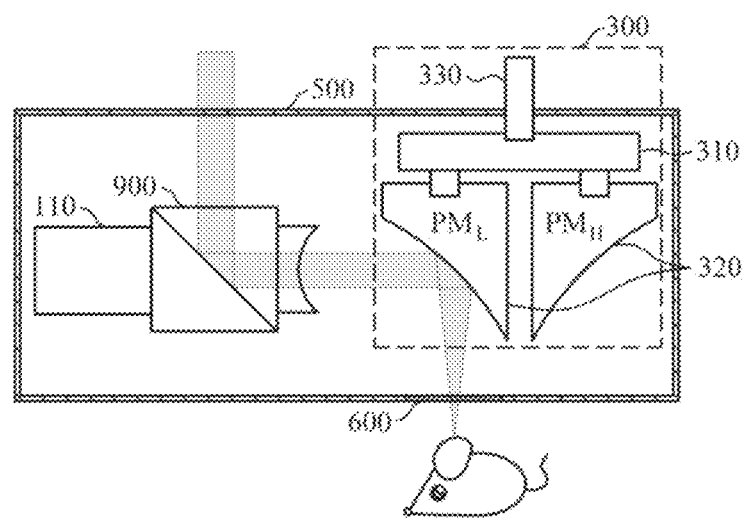
Figure 8C:
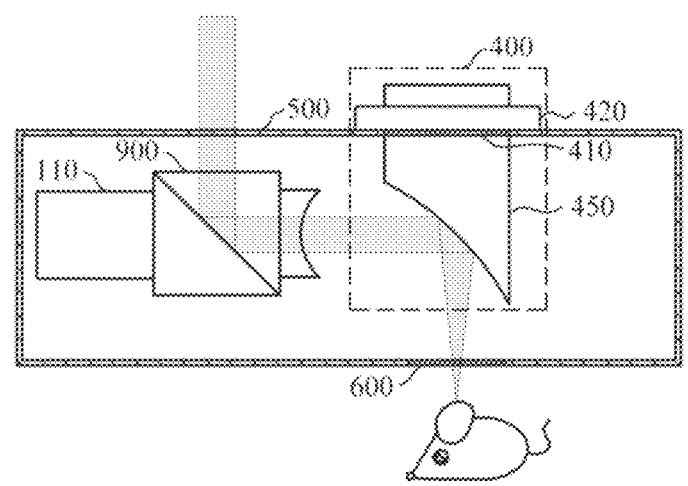

FIGS. 8A, 8B, and 8C are diagrams illustrating an example in which a photoacoustic coupling part is further included in a water tank.

Referring to FIGS. 8A to 8C, the photoacoustic apparatus 1 may include an ultrasonic transducer 110, the mirror part 200, the water tank 500, and a photoacoustic coupling part 900, among which the ultrasonic transducer 110, the mirror part 200, and the water tank 500 are described above.

The photoacoustic coupling part 900 may come into contact with the ultrasonic transducer 110. The photoacoustic coupling part 900 may reflect light, transmitted from a light source, to the mirror part 200 and may pass a photoacoustic signal, generated from the object, toward the ultrasonic transducer 110. Further, the photoacoustic coupling part 900 may align the light and ultrasonic waves along a single path, and may align the light and ultrasonic waves at the same height.

The mirror part 200 is disposed perpendicular to the transducer 110 on a light path, may reflect light, transmitted from the transducer 110, and the ultrasonic waves generated from the object, and may adjust magnification according to a desired or preset number of apertures.

Referring to FIG. 8B, a mirror part 300 according to an embodiment includes a support part 310, and a parabolic mirror set 453 of a plurality of parabolic mirrors having different magnification levels and being disposed on one surface of the support part 310. A turning part 330 may be disposed on the other surface of the support part 310, and may protrude outside of a water tank to be rotated to adjust magnification of the plurality of parabolic mirrors.

Referring to FIG. 8C, the water tank 500 has an installation hole 410, into which the parabolic mirror 450 may be inserted, and parabolic mirrors having different magnification levels may be replaceable along the installation hole 410. In this case, the parabolic mirror 450 may be coupled to the stopper 420 and may be stopped against one surface of the water tank 500 to be supported thereby.

Figure 9:
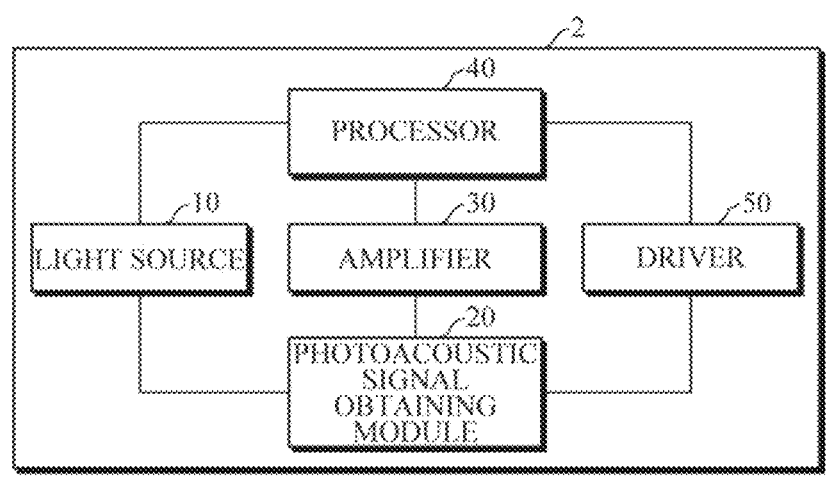
FIG. 9 is a diagram illustrating an apparatus for obtaining a photoacoustic image according to an embodiment of the present disclosure.

FIG. 9 is a diagram illustrating an apparatus for obtaining a photoacoustic image according to an embodiment of the present disclosure.

As illustrated in FIG. 9, an apparatus 2 for obtaining a photoacoustic image includes a light source 10, a photoacoustic signal obtaining module 20, an amplifier 30, a processor 40, and a driver (or a controller) 50. The photoacoustic signal obtaining module 20 may correspond to the photoacoustic apparatus 1 which is described in detail above, such that detailed description thereof will be omitted.

Light supplied from the light source 10 may be a collimator beam, but is not limited thereto. The light source 10 may include a light emitting diode (LED), a laser diode (LD), a phosphor, and the like but is not limited thereto.

The light source 10 may emit light to the photoacoustic signal obtaining module 20. The light emitted from the light source 10 is transmitted to the object, through the photoacoustic signal obtaining module 20, so that the light is to be absorbed in the object.

The amplifier 30 may amplify a photoacoustic signal by receiving the photoacoustic signal detected by the photoacoustic signal obtaining module 20. The amplifier 30 may include a pulse receiver or an radio frequency (RF) amplifier, but is not limited thereto.

The processor 40 may obtain image data by performing image processing on the signal amplified by the amplifier 30. That is, the processor 40 may finally obtain images of an inner part of the object.

The processor 40 may generate a synchronization signal to allow the light source 10 to emit light. In this case, the light source 10 may supply light according to the synchronization signal generated by the processor 40.

The driver 50 may be connected to the photoacoustic signal obtaining module and the processor 40, to drive the photoacoustic signal obtaining module 20. Further, the driver 50 may control the photoacoustic signal obtaining module 20 (or the photoacoustic apparatus 1 corresponding to the photoacoustic signal obtaining module 20) configured to adjust the magnification or resolution of photoacoustic microscopy.

Figure 10:
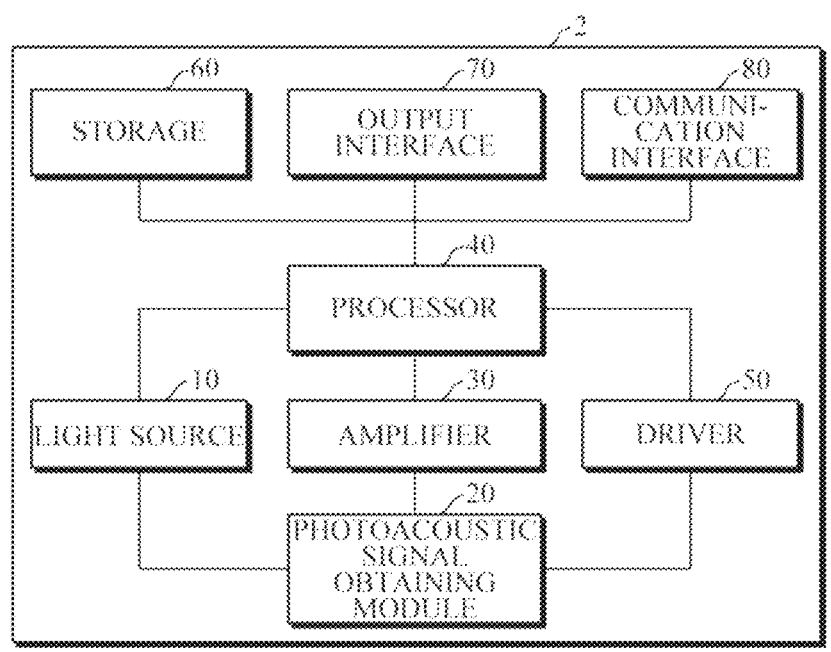
FIG. 10 is a diagram illustrating an apparatus for obtaining a photoacoustic image according to another embodiment of the present disclosure.

FIG. 10 is a diagram illustrating an apparatus for obtaining a photoacoustic image according to another embodiment of the present disclosure.

Referring to FIG. 10, the apparatus 2 for obtaining a photoacoustic image includes the light source 10, the photoacoustic signal obtaining module 20, the amplifier 30, the processor 40, the driver 50, a storage 60, an output interface 70, and a communication interface 80. The light source 10, the photoacoustic signal obtaining module 20, the amplifier 30, the processor 40, and the driver 50 are described in detail above, such that detailed description thereof will be omitted.

The storage 60 may store data, including object information, reference information such as criteria for driving a light source and the like, the obtained photoacoustic signal, the obtained photoacoustic image, and the like. The storage 60 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 70 may output data received from the processor 40. The output interface 70 may include a visual output module such as a display and the like, an audio output module such as a speaker and the like, or a haptic module using vibrations, tactile sensation, and the like.

The communication interface 80 may communicate with an external device through wired or wireless communications to receive various data from the external device. In this case, the external device may include an information processing device such as a smartphone, a tablet PC, a desktop computer, a laptop computer, and the like, but is not limited thereto.

For example, the communication interface 80 may receive the reference information, such as light source driving criteria and the like, from an external device. Further, the communication interface 80 may transmit, to the external device, a variety of information obtained, generated, and processed by the processor 40. In this case, the external device may include a smartphone, a tablet PC, a desktop computer, a laptop computer, or an information processing device of medical institutions, and the like, but is not limited thereto.

The communication interface 80 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 11:
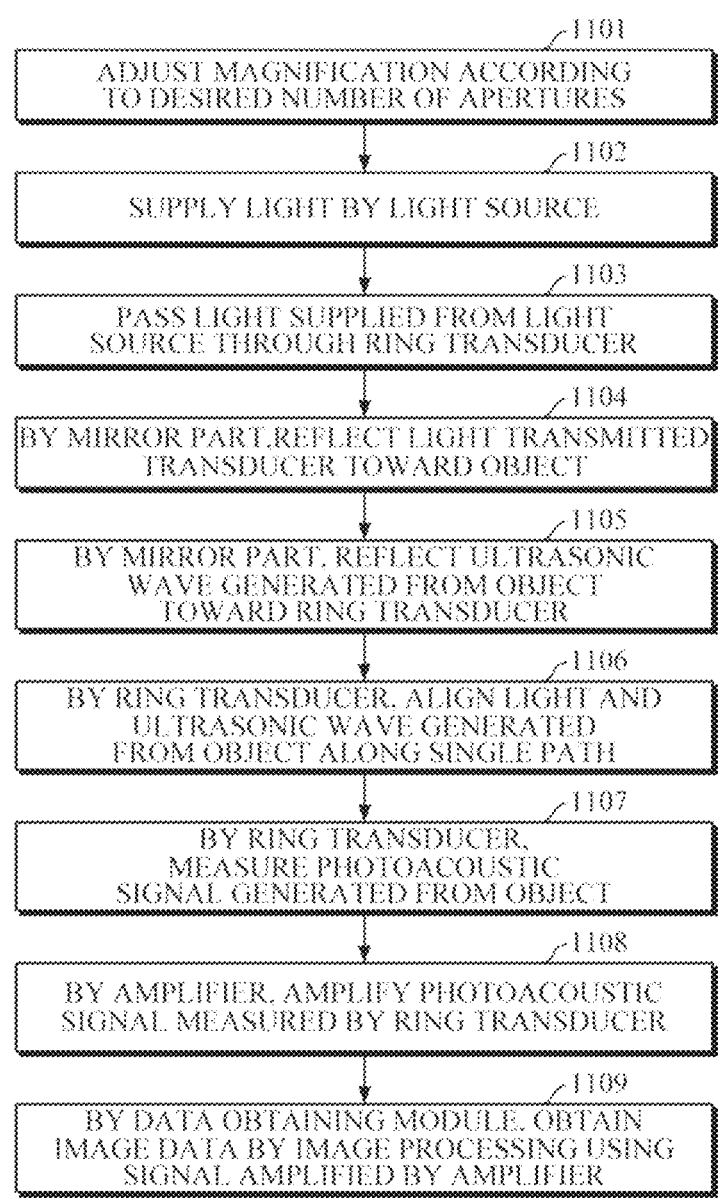
FIG. 11 is a flowchart illustrating a method of obtaining a photoacoustic image according to an embodiment of the present disclosure.

FIG. 11 is a flowchart illustrating a method of obtaining a photoacoustic image according to an embodiment of the present disclosure.

Referring to FIG. 11, magnification may be adjusted according to a desired or preset number of apertures in operation 1101. For example, a mirror part has a parabolic mirror set of a plurality of parabolic mirrors having different magnification levels, and magnification may be adjusted by rotating a parabolic mirror having a desired magnification level toward a transducer. A motor may be further coupled to the mirror part, and the parabolic mirror may be rotated by the rotation of the motor.

In another example, the parabolic mirrors having different magnification levels may be replaceable along an installation hole formed in a water tank.

Then, a light source supplies light in operation 1102, and the light supplied from the light source may pass through a ring transducer in operation 1103.

Subsequently, the mirror part may reflect light, transmitted from the ring transducer, toward the object in operation 1104, and ultrasonic waves generated from the object may be reflected to the ring transducer in operation 1105.

Further, the ring transducer may align the light and the ultrasonic waves, generated from the object, along a single path in operation 1106.

Next, the ring transducer may measure a photoacoustic signal generated from the object in operation 1107.

An amplifier may amplify the photoacoustic signal measured by the ring transducer in operation 1108.

A processor may obtain image data by image processing using the signal amplified by the amplifier in operation 1109.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD- ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A photoacoustic apparatus, comprising:
    a ring transducer configured to measure a photoacoustic signal generated from an object, and comprising a hollow space that is provided as a travel path of light and ultrasonic waves;
    a mirror part disposed along a light path of the light transmitted from the ring transducer, and configured to reflect the light transmitted from the ring transducer, and the ultrasonic waves generated from the object, and to adjust magnification of the mirror part according to a number of apertures of the photoacoustic apparatus; and
    a fluid tank comprising a transparent film that allows the photoacoustic signal to pass through the fluid tank, and accommodating a fluid, the ring transducer, and the mirror part inside the fluid tank.

2. The photoacoustic apparatus of claim 1, wherein the mirror part comprises a parabolic mirror set of a plurality of parabolic mirrors having different magnification levels and disposed on one surface of a support part of the photoacoustic apparatus.

3. The photoacoustic apparatus of claim 2, wherein the mirror part comprises a turning part disposed on another surface of the support part and protruding outside of the fluid tank, and configured to rotate to adjust the magnification of the parabolic mirror set.

4. The photoacoustic apparatus of claim 1, wherein the fluid tank comprises an installation hole, into which parabolic mirrors are inserted, and
    wherein the mirror part comprises the parabolic mirrors having different magnification levels and being replaceable through the installation hole of the fluid tank.

5. The photoacoustic apparatus of claim 4, wherein the mirror part comprises a stopper which is coupled to the parabolic mirror, and supports the parabolic mirror when the parabolic mirror is inserted into the fluid tank.

6. The photoacoustic apparatus of claim 5, wherein the stopper comprises at least one of an O-ring and a bearing to fix the parabolic mirror.

7. The photoacoustic apparatus of claim 4, further comprising a motor coupled to one surface of the mirror part outside of the fluid tank, and configured to control a position of the mirror part or to reciprocate or rotate the mirror part.

8. The photoacoustic apparatus of claim 1, further comprising a photoacoustic scanner disposed between the mirror part and the object on the light path, and configured to reflect the light transmitted from the mirror part toward the object, and to reflect the ultrasonic waves generated from the object toward the mirror part.

9. The photoacoustic apparatus of claim 1, wherein the ring transducer is a focal ring transducer having an acoustic lens to align the light and the ultrasonic waves at a same height.

10. A photoacoustic apparatus, comprising:
    an ultrasonic transducer configured to measure a photoacoustic signal generated from an object;
    a mirror part disposed along a light path of light transmitted from the ultrasonic transducer, and configured to reflect the light transmitted from the ultrasonic transducer, and the ultrasonic waves generated from the object, and to adjust magnification of the mirror part according to a number of apertures of the photoacoustic apparatus;
    a photoacoustic coupling part disposed to come into contact with the ultrasonic transducer, and configured to reflect the light transmitted from a light source toward the mirror part, and to pass the photoacoustic signal, which is generated from the object, toward the ultrasonic transducer; and
    a fluid tank comprising a transparent film that allows the photoacoustic signal to pass through the fluid tank, and accommodating a fluid, the transducer, and the mirror part inside the fluid tank.

11. An image obtaining apparatus comprising:
    a light source configured to supply light;
    a photoacoustic apparatus configured to emit the supplied light onto an object, and to detect a photoacoustic signal generated by the object after the light is absorbed into the object;
    an amplifier configured to amplify the photoacoustic signal detected by the photoacoustic apparatus;
    a processor configured to obtain image data by performing image processing on the amplified photoacoustic signal; and
    a driver configured to drive the photoacoustic apparatus,
    wherein the photoacoustic apparatus comprises:
        a ring transducer configured to transmit the light supplied from the light source, and to measure the photoacoustic signal generated from the object, and comprising a hollow space that is provided as a travel path of the light and ultrasonic waves;
        a mirror part disposed along a light path of the light transmitted from the ring transducer, and configured to reflect the light transmitted from the ring transducer, and the ultrasonic waves generated from the object, and to adjust magnification of the photoacoustic apparatus according to a number of apertures of the photoacoustic apparatus; and
        a fluid tank comprising a transparent film that allows the photoacoustic signal to pass through the fluid thank, and accommodating a fluid, the ring transducer, and the mirror part inside the fluid tank.

12. The image obtaining apparatus of claim 11, wherein the light is a collimator beam.

13. The image obtaining apparatus of claim 11, wherein the mirror part comprises a parabolic mirror set of a plurality of parabolic mirrors having different magnification levels and disposed on one surface of a support part.

14. The image obtaining apparatus of claim 13, wherein the mirror part comprises a turning part disposed on the other surface of the support part and protruding outside of the fluid tank to be rotated to adjust the magnification of the parabolic mirror set of the photoacoustic apparatus.

15. The image obtaining apparatus of claim 11, wherein the fluid tank comprises an installation hole, into which parabolic mirrors are inserted,
   wherein the mirror part comprises the parabolic mirrors having different magnification levels and being replaceable through the installation hole of the fluid tank.

16. The image obtaining apparatus of claim 15, wherein the mirror part comprises a stopper which is coupled to the parabolic mirror, such that when the parabolic mirror is inserted into the fluid tank, the stopper supports the parabolic mirror.

17. The image obtaining apparatus of claim 11, wherein the photoacoustic apparatus further comprises a motor coupled to one surface of the mirror part outside of the fluid tank, and configured to control a position of the mirror part or to reciprocate or rotate the mirror part.

18. A method of obtaining a photoacoustic image using a photoacoustic apparatus, the method comprising:
   adjusting magnification of a mirror part according to a number of apertures;
   supplying light by a light source;
   passing the light, which is supplied from the light source, through a ring transducer;
   by the mirror part, reflecting the light transmitted from the ring transducer toward an object;
   by the mirror part, reflecting ultrasonic waves generated from the object toward the ring transducer;
   by the ring transducer, aligning the light and the ultrasonic waves along a single path;
   by the ring transducer, measuring a photoacoustic signal generated from the object;
   by an amplifier, amplifying the photoacoustic signal measured by the ring transducer; and
   by a processor, obtaining image data by performing image processing on the photoacoustic signal amplified by the amplifier.

19. The method of claim 18, wherein the adjusting the magnification comprises:
   adjusting the magnification of the mirror part by rotating a turning part of the photoacoustic apparatus that is coupled to the mirror part.

20. The method of claim 18, wherein the aligning the light and the ultrasonic waves comprises aligning the light and the ultrasonic waves at a same height by using an acoustic lens included in the ring transducer.

* * * * *